United States Patent
Kim et al.

(10) Patent No.: US 10,092,605 B2
(45) Date of Patent: Oct. 9, 2018

(54) **FOOD COMPOSITION, CONTAINING *LACTOCOCCUS* STRAIN AS ACTIVE INGREDIENT, FOR ALLEVIATING HANGOVER**

(71) Applicant: CHUNG-ANG UNIVERSITY INDUSTRY-ACADEMY COOPERATION FOUNDATION, Seoul (KR)

(72) Inventors: Won Yong Kim, Seoul (KR); Woo Jin Choi, Suwon-si (KR); Maytiya Konkit, Seoul (KR); Sung Lim Cho, Gunpo-si (KR)

(73) Assignee: CHUNG-ANG UNIVERSITY INDUSTRY-ACADEMY COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/522,779

(22) PCT Filed: Oct. 29, 2015

(86) PCT No.: PCT/KR2015/011483
§ 371 (c)(1),
(2) Date: Apr. 28, 2017

(87) PCT Pub. No.: WO2016/068612
PCT Pub. Date: May 6, 2016

(65) Prior Publication Data
US 2017/0319636 A1    Nov. 9, 2017

(30) Foreign Application Priority Data

Oct. 29, 2014 (KR) .......... 10-2014-0148554
Dec. 16, 2014 (KR) .......... 10-2014-0181341

(Continued)

(51) Int. Cl.
*A61K 35/744* (2015.01)
*C12N 1/20* (2006.01)
(Continued)

(52) U.S. Cl.
CPC .......... *A61K 35/744* (2013.01); *A23C 19/076* (2013.01); *A23L 33/135* (2016.08);
(Continued)

(58) Field of Classification Search
CPC . A23L 7/104; A23L 29/00; A23L 2/00; A61K 36/65; A01N 63/00; A01N 63/02; A23C 9/123; A23C 23/00
(Continued)

(56) References Cited

FOREIGN PATENT DOCUMENTS

JP    2010-207129       *   9/2010
JP    2010-207129 A        9/2010
(Continued)

OTHER PUBLICATIONS

Liu et al., (J Biotechnol. Dec. 15, 2012;164(2):188-95. doi: 10.1016/j.jbiotec.2012.08.008. Epub Sep. 3, 2012).*
(Continued)

*Primary Examiner* — Jana A Hines
(74) *Attorney, Agent, or Firm* — Revolution IP, PLLC

(57) ABSTRACT

A food composition for alleviating hangovers, the food composition contains, as an active ingredient, at least one strain selected from the group consisting of *Lactococcus chungangensis, Lactococcus fujiensis, Lactococcus lactis* subsp. *cremoris, Lactococcus lactis* subsp. *lactis*, and *Lactococcus raffinolactis*, or a culture liquid thereof culture medium, wherein functional cream cheese is prepared using five species of *Lactococcus* strains above having the ability to decompose ethanol and acetaldehyde.

12 Claims, 9 Drawing Sheets

*L. chungangensis*    *L. fujiensis*    *L. lactis subsp. cremoris*

*L. lactis subsp. lactis*    *L. raffinolactis*

(30) Foreign Application Priority Data

Dec. 16, 2014 (KR) .................. 10-2014-0181342
Dec. 16, 2014 (KR) .................. 10-2014-0181343
Dec. 16, 2014 (KR) .................. 10-2014-0181344

(51) Int. Cl.
*A23C 19/076* (2006.01)
*A23L 33/00* (2016.01)
*A23L 33/135* (2016.01)
*A61K 35/00* (2006.01)

(52) U.S. Cl.
CPC .............. *A23L 33/30* (2016.08); *C12N 1/20* (2013.01); *A23V 2002/00* (2013.01); *A61K 2035/11* (2013.01)

(58) Field of Classification Search
USPC .......... 435/170; 424/93.45, 780; 426/61, 71, 426/590
See application file for complete search history.

(56) References Cited

FOREIGN PATENT DOCUMENTS

| KR | 10-0663086 A | 1/2007 | | |
|---|---|---|---|---|
| KR | 10-2010-0017206 A | 2/2010 | | |
| KR | 10-2013-0086660 A | 8/2013 | | |
| KR | 10-1371648 | * | 8/2013 | .............. C12N 1/20 |
| KR | 10-2013-0100036 A | 9/2013 | | |
| KR | 10-1333758 B1 | 11/2013 | | |
| KR | 10-1371648 B1 | 3/2014 | | |

OTHER PUBLICATIONS

Park et al., (Curr. Microbiol. 2003. 46(5):385-8).*

International Search Report for PCT/KR2015/011483 dated Feb. 26, 2016 from Korean Intellectual Property Office.

Konkit, M et al., "Transcriptomic analysis of *Lactococcus chungangensis* sp. nov. and its potential in cheese making", J. Dairy Sci. Epub. Oct. 11, 2014, vol. 97, No. 12, pp. 7363-7372.

Mengjin Liu, et al., "Comparative Genomics of Enzymes in Flavor-Forming Pathways from Amino Acids in Lactic Acid Bacteria", Applied and Environmental Microbiology, Aug. 2008, p. 4590-4600.

* cited by examiner

FOOD COMPOSITION, CONTAINING *LACTOCOCCUS* STRAIN AS ACTIVE INGREDIENT, FOR ALLEVIATING HANGOVER

CROSS REFERENCE TO PRIOR APPLICATIONS

This application is a National Stage Application of PCT International Patent Application No. PCT/KR2015/011483 filed on Oct. 29, 2015, under 35 U.S.C. § 371, which claims priority to Korean Patent Application Nos. 10-2014-0148554 filed on Oct. 29, 2014, 10-2014-0181341 filed on Dec. 16, 2014, 10-2014-0181342 filed on Dec. 16, 2014, 10-2014-0181343 filed on Dec. 16, 2014, and 10-2014-0181344 filed on Dec. 16, 2014, which are all hereby incorporated by reference in their entirety.

TECHNICAL FIELD

The present invention relates to a food composition for alleviating hangovers, the food composition containing, as an active ingredient, at least one strain selected the group consisting of *Lactococcus chungangensis, Lactococcus fujiensis, Lactococcus lactis* subsp. *cremoris, Lactococcus lactis* subsp. *lactis*, and *Lactococcus raffinolactis*, or a culture medium thereof.

BACKGROUND ART

Cheese is a fermented food known to human beings for thousands of years. Today, more than 1,400 kinds of cheese are known. Based on records of foods similar to cheese in Mesopotamia around 6000 BC, cheese is presumed to have an ancient origin. In addition, it is believed that cheese has been used since ancient times because there is an excavation of wooden apparatuses for making cheese during the Cortaillod culture in Swiss around 3000 BC or the Minoan civilization of Crete island in Crete, Switzerland, around 3000 BC. Despite 1,400 kinds of cheese, some cheeses are similar to each other while other cheeses are very different from each other, depending on shape, size, aging period, crude oil used, additive, packaging method, and production area. The Codex *Alimentarius* Commission continues to review and revise the quality standard of cheese to be produced. Cheese generally contains 20% to 30% of proteins and fats, and cottage cream cheese has a greater fat content than protein. Cheese that has been aged contains ingredients that are changed into a form being easily digested or absorbed due to the influence of enzymes such as lactic acid bacteria. In addition, cheese is also rich in minerals, such as calcium, phosphorus, and sulfur, and vitamins A and B, and thus is good for beauty care. Cheese is a fermented food that is highly recommended as a nutritious food for patients with weak digestive system of elderly people as well as growing children.

Cream cheese, as its name implies, is creamy cheese that does not have the nature of cheese with unpleasant taste and smell. Cream cheese is in the form of white soft creamy lumps, has a sweet and sour flavor that can be tasted during the fermentation process of yogurt, and is characterized by soft texture. Cream cheese is made by warming and separating curd produced by adding a curdling enzyme and a starter containing various lactic acid bacteria, and thus has a high moisture content and is difficult to store. In this regard, cream cheese produced in this way is sold at a high cost.

Hangovers that a person may feel the next day after drinking can not only ruin physical health, but also diminish the quality of life. On the next day after drinking, most people suffer from soreness, vomiting, and severe headaches. There is a slight difference in alcohol, but based on soju, soju has a calorie of 7.1 kcal per 1 gram ethanol and contains few other nutrients. Only 2% to 10% of ethanol absorbed through drinking is excreted via exhaled breath or in the urine through the kidney or lungs, and more than 90% of the remaining ethanol is rapidly metabolized in the liver. Ethanol decomposed in the liver produced acetaldehyde which in turn is converted to acetic acid to be decomposed into water and carbon dioxide. Acetaldehyde produced herein causes hangovers including a reddening face, a pounding heart, headaches, and stomach pain. Frequent drinking is a major cause of great burden on the liver that breaks down alcohol.

To alleviate such hangovers after drinking, bean sprouts, dried pollack, mung beans, or the like have been used from old times as foods for alleviating hangovers after drinking. In addition, many foods related to hangover cures are known, but such foods are dependent on raw materials and efficacy known in the folk remedies or described in the classic oriental medicine books, and thus there is a lack of scientific approach.

DETAILED DESCRIPTION OF THE INVENTION

Technical Problem

The present invention provides a food composition for alleviating hangovers, the food composition containing, as an active ingredient, at least one strain selected from the group consisting of *Lactococcus chungangensis, Lactococcus fujiensis, Lactococcus lactis* subsp. *cremoris, Lactococcus lactis* subsp. *lactis*, and *Lactococcus raffinolactis*, or a culture medium thereof.

Technical Solution

The present invention provides a food composition for alleviating hangovers, the food composition containing, as an active ingredient, at least one strain selected from the group consisting of *Lactococcus chungangensis, Lactococcus fujiensis, Lactococcus lactis* subsp. *cremoris, Lactococcus lactis* subsp. *lactis*, and *Lactococcus raffinolactis*, or a culture medium thereof.

The present invention also provides a method of preparing cream cheese for alleviating hangovers, the method including culturing at least one strain selected from the group consisting of *Lactococcus chungangensis, Lactococcus fujiensis, Lactococcus lactis* subsp. *cremoris, Lactococcus lactis* subsp. *lactis*, and *Lactococcus raffinolactis*, and mixing the cultured strain(s) with milk.

Advantageous Effects of the Invention

The present invention relates to a food composition for alleviating hangovers, the food composition containing, as an active ingredient, at least one strain selected from the group consisting of *Lactococcus chungangensis, Lactococcus fujiensis, Lactococcus lactis* subsp. *cremoris, Lactococcus lactis* subsp. *lactis*, and *Lactococcus raffinolactis*, or a culture medium thereof. Specifically, functional cream cheese is prepared using five species of *Lactococcus* strains above having the ability to decompose ethanol and acetaldehyde. Such functional cream cheese is preferably used for a functional health food for alleviating hangovers, and extensively, acetaldehyde, which is an ethanol decomposition product, is decomposed to minimize the accumulation of acetaldehyde that may cause cancer in the body. In addition, the functional cream cheese, as a cheese starter for lowering a unit cost compared with cream cheese available in the market, can be differentiated from cream cheeses sold in the market.

BEST MODE

Figure 1:
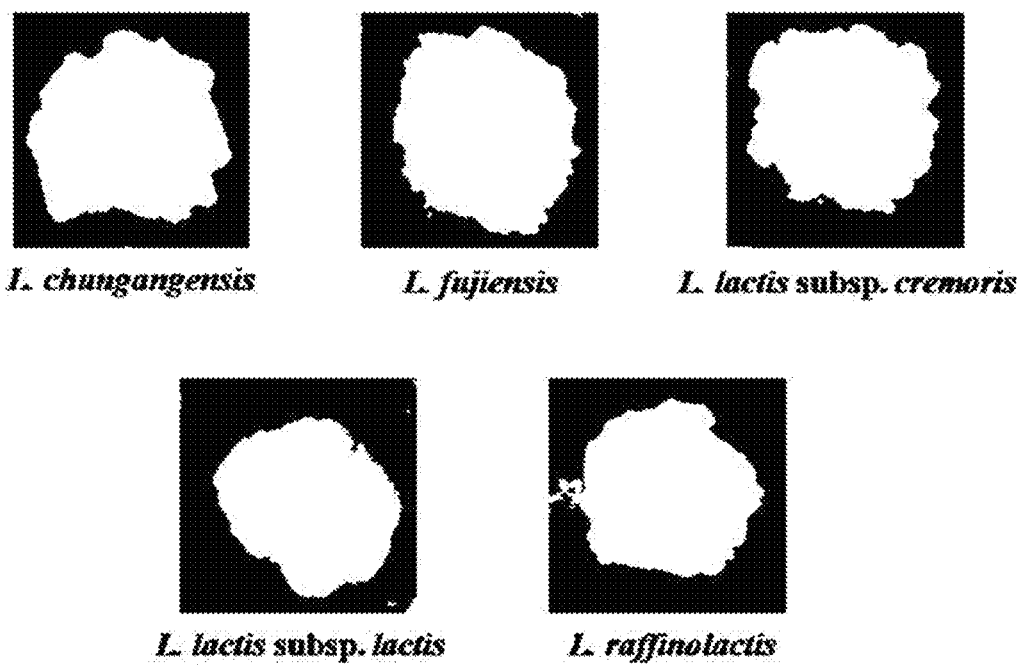
FIG. 1 shows images of cream cheese prepared using *Lactococcus chungangensis, Lactococcus fujiensis, Lactococcus lactis* subsp. *cremoris, Lactococcus lactis* subsp. *lactis*, or *Lactococcus raffinolactis*.

In the present invention, *Lactococcus chungangensis, Lactococcus fujiensis, Lactococcus lactis* subsp. *cremoris, Lactococcus lactis* subsp. *lactis*, or *Lactococcus raffinolactis*, each of which has the ability to decompose ethanol and acetaldehyde, is used to prepare functional cream cheese, and such functional cream cheese is preferably used for a functional health food for alleviating hangovers. Extensively, acetaldehyde, which is an ethanol decomposition product, is decomposed to minimize the accumulation of acetaldehyde that may cause cancer in the body. In addition, the functional cream cheese, as a cheese starter for lowering a unit cost compared with cream cheese available in the market, can be differentiated from cream cheeses sold in the market.

The present invention provides a food composition for alleviating hangovers, the food composition containing, as an active ingredient, at least one strain selected from the group consisting of *L. chungangensis, L. fujiensis, L. lactis* subsp. *cremoris, L. lactis* subsp. *lactis*, and *L. raffinolactis*, or a culture medium thereof.

Preferably, the culture medium may be cultured at a temperature of 25° C. to 37° C. for 24 hours to 48 hours, but embodiments are not limited thereto.

In detail, the food composition having the ability to decompose ethanol or acetaldehyde may alleviate hangovers.

The food composition disclosed in the present invention may contain, as an active ingredient, a viable or dried cell of *Lactococcus chungangensis, Lactococcus fujiensis, Lactococcus lactis* subsp. *cremoris, Lactococcus lactis* subsp. *lactis*, or *Lactococcus raffinolactis*, a culture medium thereof, or a fermented product thereof, wherein the culture medium or the fermented product may include a culture medium itself in which the above-mentioned five species of *Lactococcus* strains are cultured in an suitable liquid medium, or a filtrate (filtered liquid or supernatant obtained by centrifugation) from which the strains are removed by performing filtration or centrifugation on the culture medium. However, embodiments are not limited thereto.

In addition, the disclosure of the present invention can be utilized as a food or a fermented product, and types of such a food or a fermented product are not particularly limited. Examples of the food are meet, sausage, bread, chocolates, candies, snacks, cookies, pizza, ramen noodles, other noodles, gums, dairy products including ice cream, various soups, beverages, tea, drinks, alcoholic drinks, and vitamin complex. Examples of the fermented product include fermented meat products such as ham and sausage, fermented reproductive products, fermented milk products, and kimchi. A fermented product using lactic acid bacteria of the present invention may be prepared according to a conventional method known in the art. Preferably, according to an embodiment of the present invention, the food may be cheese, specifically cream cheese, but embodiments are not limited thereto.

The term "starter" used in the present invention refers to a microbial culture medium used when preparing a fermented product. Therefore, types of starter microorganisms determine characteristics of a product to be prepared, and also have an important influence on the quality of the product. Bacteria, fungi, and yeast are examples of the starter microorganisms, and can be used alone or in combination.

In addition, the present invention provides a method of preparing cream cheese for alleviating hangovers, the method including: (1) culturing at least one strain selected from the group consisting of *L. chungangensis, L. fujiensis, L. lactis* subsp. *cremoris, L. lactis* subsp. *lactis*, and *L. raffinolactis*, or a culture medium thereof, by inoculation into milk; (2) performing pasteurization on the culture cultured in step (1); (3) mixing the pasteurized culture with milk and heating the mixture; and (4) removing moisture from cheese obtained by the heating of the mixture.

MODE OF THE INVENTION

Hereinafter, the present invention will be described in detail with reference to Examples which do not limit the present invention. The following Examples of the present invention are for illustrative purposes only, and do not limit the scope of the present invention. Therefore, it is to be understood that what is easily inferred by one of ordinary skill in the art based on the detailed description and Examples of the present invention is construed as belonging to the scope of the present invention.

<Experimental Examples>

Following Experimental Examples are intended to provide experimental examples that are commonly applied to each Example according to the present invention.

1. Culture of *L. chungangensis, L. Fujiensis, L. lactis* Subsp. *Cremoris, L. lactis* subsp. *lactis*, or *L. raffinolactis*

*L. chungangensis*, which is a strain isolated in the present laboratory, was isolated from activated sludge bubbles. The strain was deposited at the Korean Collection for Type Cultures (KCTC).

*L. fujiensis* (KCTC3185$^T$) distributed from the KCTC was used.

*L. lactis* subsp. *cremoris* (KCCM40699) distributed from the Korean Culture Center of Microorganisms (KCCM) was used.

*L. lactis* subsp. *lactis* (KCTC3769$^T$) distributed from the KCTC was used.

*L. raffinolactis* (DSM20443$^T$) distributed from the Deutsche Sammlung von Mikroorganismen (DSM) was used.

*L. chungangensis, L. fujiensis, L. lactis* subsp. *cremoris, L. lactis* subsp. *lactis*, or *L. raffinolactis* was inoculated into a tryptic soy broth (TSB) medium, and then, cultured in a shaking incubator at 30° C. for 24 hours. Here, cell density of each strain was measured using a microplate reader (model Infinite° F.200, Tecan, Mannedorf, Switzerland), and each of the strains was inoculated into acidified milk at a concentration of $4 \times 10^8$ cells.

2. Preparation of Cream Cheese Using *L. Chungangensis, L. Fujiensis, L. Lactis* Subsp. *Cremoris, L. Lactis* Subsp. *Lactis*, or *L. Raffinolactis*

Lactic acid bacterium used as a starter for cream cheese, such as *L. chungangensis, L. fujiensis, L. lactis* subsp. *cremoris, L. lactis* subsp. *lactis*, or *L. raffinolactis*, was inoculated into acidified milk, and then, cultured for 48 hours. Following the incubation, the cultured product was mixed with milk, which was prepared by performing pasteurization thereon at 68° C. for 30 minutes and cooling off the pasteurized milk, and then, heated at 70° C. for 5 minutes. To remove moisture from cheese produced after the heating of the cultured product, only curd was obtained using a fabric. 0.5% salt was used to remove moisture, thereby completing the preparation of cheese (see FIG. 1). Cheese obtained therefrom was subjected to lyophilization for storage in powder form, and then, stored at 4° C. until further experiments were carried out.

3. Culture of *L. garvieae, L. lactis* Subsp. *Hordiniae, L. lactis* Subsp. *Tructae*, and *L. taiwanensis*

*L. garvieae* (KCTC3772$^T$) and *L. lactis* subsp. *hordiniae* (KCTC3768) distributed from the KCTC were used. *L. lactis* subsp. *tructae* (NBRC110453) and *L. taiwanensis* (NBRC109049) distributed from the National Biological Resource Center (NBRC) were used.

*L. garvieae, L. lactis* subsp. *hordiniae, L. lactis* subsp. *tructae*, and *L. taiwanensis* were each inoculated into a TSB medium, and then, cultured in a shaking incubator at 30° C. for 24 hours. Here, cell density of each strain was measured using a microplate reader (model Infinite®F200, Tecan, Mannedorf, Switzerland), and each of the strains was inoculated into acidified milk at a concentration of $4 \times 10^8$ cells.

4. Preparation of Cream Cheese Using L. Garvieae, *L. lactis* Subsp. *Hordiniae, L. lactis* Subsp. *Tructae*, and *L. taiwanensis*

Lactic acid bacterium used as a starter for cream cheese, such as L. garvieae, *L. lactis* subsp. *hordiniae, L. lactis* subsp. *tructae*, and *L. taiwanensis*, was inoculated into acidified milk, and then, cultured for 48 hours. Following the incubation, the cultured product was mixed with milk, which was prepared by performing pasteurization thereon at 68° C. for 30 minutes and cooling off the pasteurized milk, and then, heated at 70° C. for 5 minutes. However, the strains above were unable to produce curd for preparing cheese, resulting in failure of the preparation of cream cheese.

5. Measurement of Fatty Acid in Cream Cheese by Gas Chromatography

According to the experimental method above, volatile fatty acids were detected from cream cheese using each of *L. chungangensis, L. fujiensis, L. lactis* subsp. *cremoris, L. lactis* subsp. *lactis*, and *L. raffinolactis*, and yields thereof were compared. Here, the cream cheese was lyophilized, followed by being finely ground. 340 µl of a methylation mixture (MeOH:Benzen:DMP:$H_2SO_4$=39:20:5:2) and 200 µl of heptane were added and stirred with the cream cheese, and an extraction process was performed thereon at 80° C. for 2 hours to obtain fatty acids. The analysis of organic acids was carried out according to gas chromatography using a flame ionization detector (FID). A column used herein was DB-Wax (Agilent, 30 mm*0.25 mm*0.25 um), and analysis conditions were as follows: the oven temperature was increased by 25° C. per minute, thereby raising from 50° C. to 230° C., and the temperature of an inlet and a detector was set at 250° C.

6. Cytotoxicity Assay on RAW 264.7 Cells in Cream Cheese

The cytotoxicity measurement was performed on the cream cheese obtained above. Mouse macrophages, i.e., RAW 264.7 cells, were used for cytotoxicity measurement experiments. The RAW 264.7 cells were subcultured three to four times a week, and a medium used herein was Dulbecco's Modified Eagle's Medium (DEME) supplemented with 20 µg/ml gentamicin and 10% fetal bovine serum (FBS), thereby culturing the RAW 264.7 cells at 37° C. in a 5% $CO_2$ environment. The cultured cells were then distributed into a 96-well plate, and then, cultured at a concentration of $1 \times 10^5$ cells/well for 24 hours. In addition, cream cheese, which was melted in a new FBS-free DMEM to have a final concentration of 10 mg/ml, was treated with cell strains, and then, the cell strains were cultured for 24 hours. To measure the viability of the cell strains, the absorbance was measured at 590 nm with a microplate reader using a 3-(4,5-dimethylthiazol-2-yl)-2, 5-diphenyltetrazolium bromide (MTT) reagent. In addition, to measure the cell damage, measurement of enzyme, such as lactate dehydrogenase (LDH), was performed. The amount of LDH released from the cells was measured at 430 nm with a microplate reader.

7. Measurement of Alcohol Dehydrogenase (ADH) and Acetaldehyde Dehydrogenase (ALDH) Activity in Culture Containing *L. chungangensis, L. Fujiensis, L. lactis* Subsp. *Cremoris, L. Lactis* Subsp. *Lactis*, or *L. raffinolactis*

Regarding a culture containing *L. chungangensis, L. fujiensis, L. lactis* subsp. *cremoris, L. lactis* subsp. *lactis*, or *L. raffinolactis* being selected from the above and having no cytotoxicity, the ability of the strains to decompose alcohol and acetaldehyde was measured according to the following method. The measurement of ADH activity in a culture containing lactic acid bacteria was performed by modifying the methods of Lebsack and Bostian. The ADH activity was measured by measuring the absorbance at 340 nm with a microplate reader and comparing the measurements with relative activity of a control group. Here, the control group was subjected to comparative analysis using ADH. Regarding compositions of a reaction solution, 1.0 M Tris/HCl buffer (pH 8.8), 20 mM NAD⁺, 0.2 M ethanol, and distilled water were added to have a total volume of 3 ml, and then, reacted in a 30° C. constant-temperature water bath for 5 minutes. The supernatant was recovered after the reaction, and the absorbance thereof was measured at 340 nm. The measurement of ALDH activity in a culture containing lactic acid bacteria was performed by modifying the method of Tottmar. The ALDH activity was also measured by measuring the absorbance at 340 nm with a microplate reader and comparing the measurements with relative activity of a control group. Here, the control group was subjected to comparative analysis using ALDH. Regarding compositions of a reaction solution, 1.0 M Tris/HCl buffer (pH 8.0), 20 mM NAD⁺, 3.0 M KCl, 0.33 M 2-mercaptoehanol, 1.0 M acetaldehyde, and distilled water were added to have a total volume of 3 ml, and then, reacted in a 30° C. constant-temperature water bath for 5 minutes. The supernatant was recovered after the reaction, and the absorbance thereof was measured at 340 nm.

8. Measurement of ADH and ALDH Activity in Cream Cheese

Regarding cream cheese being selected from the above and having no cytotoxicity, the ability of the cream cheese to decompose alcohol and acetaldehyde was also measured according to the method in the same manner as the method for measuring the culture containing lactic acid bacteria.

9. Measurement of Concentrations of Alcohol and Acetaldehyde in Mouse by Oral Administration of Cream Cheese Prepared Using *L. Chungangensis, L. Fujiensis, L. lactis* Subsp. *Cremoris, L. Lactis* Subsp. *Lactis*, or *L. raffinolactis*

In the present invention, a 5-week-old imprinting control region (ICR) mouse purchased from SAMTAKO (Osan, Gyeonggi-do) was preliminarily fed with solid feed and water for a week, and then, experiments were carried out. To investigate the effect of cream cheese prepared using *L. chungangensis, L. fujiensis, L. lactis* subsp. *cremoris, L. lactis* subsp. *lactis*, or *L. raffinolactis*, which was selected from the above and had excellent ability to decompose alcohol and acetaldehyde, on alcoholic hangovers, the concentrations of blood alcohol and acetaldehyde were measured according to the passage of time (1, 3, 5, and 7 hours) after alcohol consumption of the mouse. Animal experiments were carried out in a normal group in which distilled water was orally administered into a mouse, a control group in which alcohol was orally administered into a mouse, and an experimental group in which alcohol and cream cheese prepared using *L. chungangensis, L. fujiensis, L. lactis* subsp. *cremoris, L. lactis* subsp. *lactis*, or *L. raffinolactis* were orally administered into a mouse, wherein each group consist of 10 mice. Regarding alcohol consumption, 22% alcohol (15 ml/kg body wt.) was orally administered, and in a positive control group, alcohol and cream cheese (100 mg/kg body wt.) preparing using *L. chungangensis, L. fujiensis, L. lactis* subsp. *cremoris, L. lactis* subsp. *lactis*, or *L. raffinolactis* were orally administered together. Blood was collected 1 hour, 3 hours, 5 hours, and 7 hours after administration, was left at room temperature for 30 minutes and at 4° C. for 10 minutes, and then, was subjected to centrifugation at a speed of 1,500 rpm for 15 minutes to separate the supernatant. 0.3 M potassium phosphate buffer (pH 9.0) and 49 mM NAD⁺ were mixed together, and a blood sample was added to the mixture. A reaction of the mixture was allowed at 20° C. for 5 minutes, and the absorbance thereof was measured at 340 nm with a microplate reader (A1). In addition, ADH or ALDH 50 was added to the mixture for a reaction allowed at 20° C. for 5 minutes, and the absorbance thereof was measured at 3409 nm (A2). Accordingly, the concentration of blood alcohol was quantified by the following formula:

Concentration=0.7259/3.6×ΔA

ΔA=sample(A2−A1)−blank(A2−A1)

In addition, the concentration of blood acetaldehyde was quantified by the following formula:

Concentration=0.7158/3.6×ΔA

ΔA=sample(A2−A1)−blank(A2−A1)

EXAMPLES

1. Fatty Acid Analysis Using Gas Chromatography on Cream Cheese Prepared Using *L. chungangensis, L. Fujiensis, L. lactis* Subsp. *Cremoris, L. Lactis* Subsp. *Lactis*, or *L. raffinolactis*

As a result of using gas chromatography to analyze fatty acid compositions of cream cheese preparing using *L. chungangensis*, methyl palmitate was found the most, followed by oleic acid, methyl pentadecanoate, octadecanoic acid, and methyl myristate, in this stated order. Ratios of the compositions above can determine the flavor of cream cheese prepared using *L. chungangensis* (see Table 1).

TABLE 1

| Flavor compounds Flavor compounds | Cream cheese prepared using *L. chungangensis* (mg/g) |
|---|---|
| Octanoic acid | 1.50 |
| Methyl decanoate | 3.96 |
| Methyl laurate | 6.82 |
| Methyl myristate | 19.93 |
| Methyl myristoleate | 1.30 |
| Methyl pentadecanoate | 30.03 |
| Methyl palmitate | 56.00 |
| Methyl palmitoleate | 2.22 |
| Octadecanoic acid | 26.88 |
| Oleic acid | 40.65 |
| Linoleic acid | 4.31 |
| Linolenic acid | 0.31 |
| Methyl heneicosanoate | 0.38 |
| cis-8,11,14-Eicosatrieonic acid methyl ester | 0.29 |
| cis-11,14,17-Eicosatrienoic acid methyl ester | 0.25 |

As a result of using gas chromatography to analyze fatty acid compositions of cream cheese preparing using *L. fujiensis*, methyl pentadecanoate was found the most, followed by methyl palmitate, oleic acid, octadecanoic acid, and methyl myristate, in this stated order. Ratios of the compositions above can determine the flavor of cream cheese prepared using *L. fujiensis* (see Table 2).

TABLE 2

| Flavor compounds Flavor compounds | Cream cheese prepared using *L. fujiensis* (mg/g) |
|---|---|
| Octanoic acid | 0.91 |
| Methyl decanoate | 2.12 |
| Methyl laurate | 3.77 |
| Methyl myristate | 10.80 |
| Methyl myristoleate | 0.74 |
| Methyl pentadecanoate | 34.25 |
| Methyl palmitate | 30.36 |
| Methyl palmitoleate | 1.18 |

TABLE 2-continued

| Flavor compounds | Cream cheese prepared using L. fujiensis (mg/g) |
|---|---|
| Octadecanoic acid | 14.50 |
| Oleic acid | 22.72 |
| Linoleic acid | 2.26 |
| Linolenic acid | 0.19 |
| Methyl heneicosanoate | 0.21 |
| cis-8,11,14-Eicosatrieonic acid methyl ester | 0.21 |
| cis-11,14,17-Eicosatrienoic acid methyl ester | 0.19 |

As a result of using gas chromatography to analyze fatty acid compositions of cream cheese preparing using *L. lactis* subsp. *cremoris*, methyl palmitate was found the most, followed by oleic acid, methyl pentadecanoate, octadecanoic acid, and methyl myristate, in this stated order. Ratios of the compositions above can determine the flavor of cream cheese prepared using *L. lactis* subsp. *cremoris* (see Table 3).

TABLE 3

| Flavor compounds | Cream cheese prepared using L. lactis subsp. cremoris (mg/g) |
|---|---|
| Octanoic acid | 1.26 |
| Methyl decanoate | 3.16 |
| Methyl laurate | 5.62 |
| Methyl myristate | 16.33 |
| Methyl myristoleate | 1.10 |
| Methyl pentadecanoate | 25.91 |
| Methyl palmitate | 45.91 |
| Methyl palmitoleate | 1.87 |
| Octadecanoic acid | 21.83 |
| Oleic acid | 34.41 |
| Linoleic acid | 3.45 |
| Linolenic acid | 0.32 |
| Methyl heneicosanoate | 0.32 |
| cis-8,11,14-Eicosatrieonic acid methyl ester | 0.26 |
| cis-11,14,17-Eicosatrienoic acid methyl ester | 0.23 |

As a result of using gas chromatography to analyze fatty acid compositions of cream cheese preparing using *L. lactis* subsp. *lactis*, methyl palmitate was found the most, followed by oleic acid, methyl pentadecanoate, octadecanoic acid, and methyl myristate, in this stated order. Ratios of the compositions above can determine the flavor of cream cheese prepared using *L. lactis* subsp. *lactis* (see Table 4).

TABLE 4

| Flavor compounds | Cream cheese prepared using L. lactis subsp. lactis (mg/g) |
|---|---|
| Octanoic acid | 1.15 |
| Methyl decanoate | 2.72 |
| Methyl laurate | 4.89 |
| Methyl myristate | 14.26 |
| Methyl myristoleate | 0.96 |
| Methyl pentadecanoate | 21.98 |
| Methyl palmitate | 40.30 |
| Methyl palmitoleate | 1.60 |
| Octadecanoic acid | 19.29 |
| Oleic acid | 29.91 |
| Linoleic acid | 2.71 |
| Linolenic acid | 0.25 |

TABLE 4-continued

| Flavor compounds | Cream cheese prepared using L. lactis subsp. lactis (mg/g) |
|---|---|
| Methyl heneicosanoate | 0.28 |
| cis-8,11,14-Eicosatrieonic acid methyl ester | 0.21 |
| cis-11,14,17-Eicosatrienoic acid methyl ester | 0.15 |

As a result of using gas chromatography to analyze fatty acid compositions of cream cheese preparing using *L. raffinolactis*, methyl pentadecanoate was found the most, followed by methyl palmitate, oleic acid, octadecanoic acid, and methyl myristate, in this stated order. Ratios of the compositions above can determine the flavor of cream cheese prepared using *L. raffinolactis* (see Table 5).

TABLE 5

| Flavor compounds | Cream cheese prepared using L. raffinolactis (mg/g) |
|---|---|
| Octanoic acid | 0.91 |
| Methyl decanoate | 2.18 |
| Methyl laurate | 3.84 |
| Methyl myristate | 11.17 |
| Methyl myristoleate | 0.77 |
| Methyl pentadecanoate | 35.84 |
| Methyl palmitate | 31.43 |
| Methyl palmitoleate | 1.22 |
| Octadecanoic acid | 15.01 |
| Oleic acid | 22.90 |
| Linoleic acid | 2.31 |
| Linolenic acid | 0.20 |
| Methyl heneicosanoate | 0.22 |
| cis-8,11,14-Eicosatrieonic acid methyl ester | 0.15 |
| cis-11,14,17-Eicosatrienoic acid methyl ester | 0.16 |

2. Cytotoxicity Assay on RAW 264.7 Cells Treated with Cream Cheese Prepared Using *L. chungangensis, L. Fujiensis, L. lactis* Subsp. *Cremoris, L. Lactis* Subsp. *Lactis*, or *L. raffinolactis*

Figure 2A:
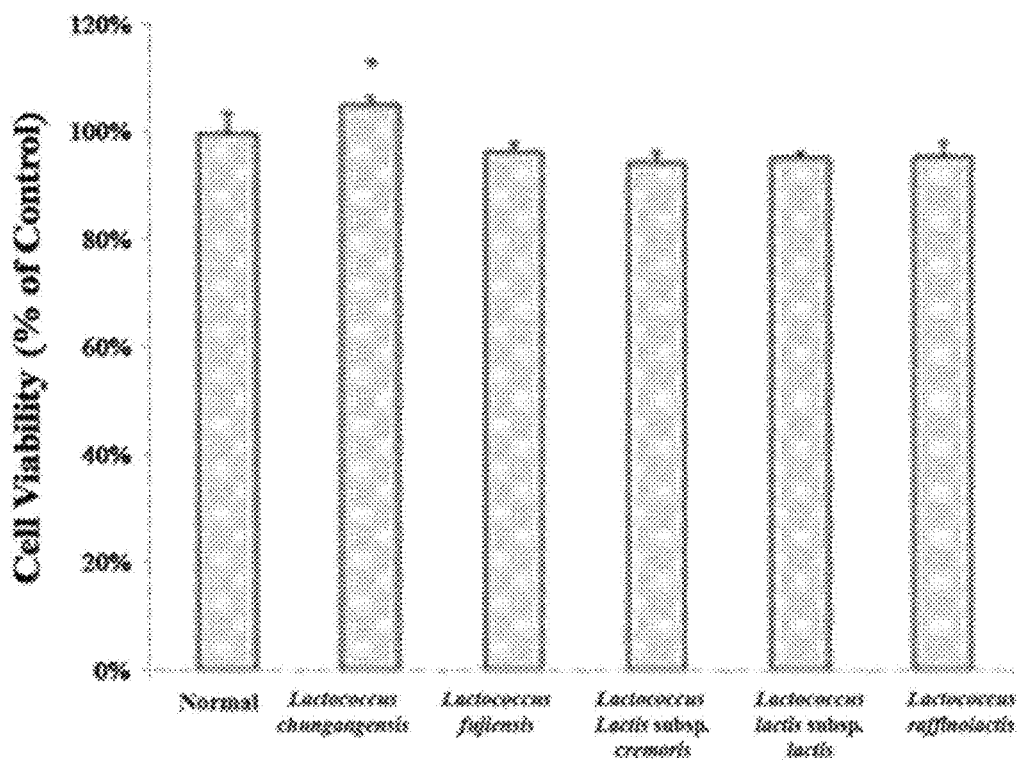
FIGS. 2A and 2B are graphs showing cytotoxicity analysis results obtained by treating mouse macrophage RAW 264.7 cells with cream cheese prepared using *L. chungangensis, L. fujiensis, L. lactis* subsp. *cremoris, L. lactis* subsp. *lactis*, or *L. raffinolactis*.
Figure 2B:
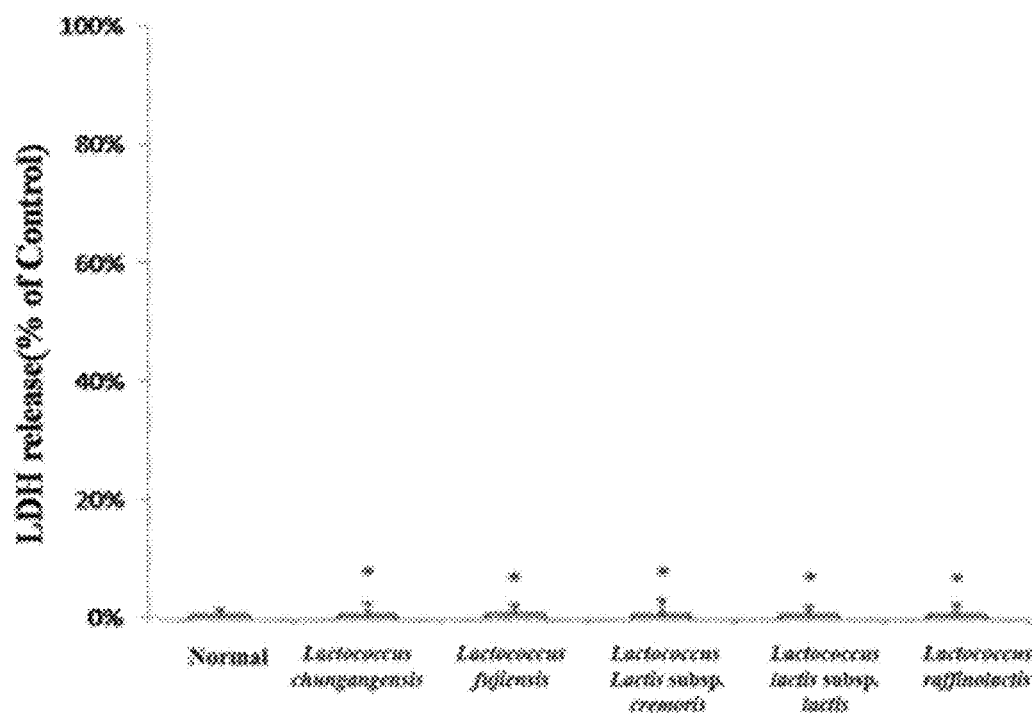

It was confirmed that the viability of RAW 264.7 cells treated with cream cheese prepared using *L. chungangensis, L. fujiensis, L. lactis* subsp. *cremoris, L. lactis* subsp. *lactis*, or *L. raffinolactis* did not decrease, and that the amount of lactate dehydrogenase (LDH) released from the cells was significantly low so that there was no cell damage. Therefore, it was also confirmed that cream cheese prepared using *L. chungangensis, L. fujiensis, L. lactis* subsp. *cremoris, L. lactis* subsp. *lactis*, or *L. raffinolactis* had no cytotoxicity (see FIG. 2).

3. Measurement of ADH and ALDH Activity in Culture Containing *L. Chungangensis, L. Fujiensis, L. lactis* Subsp. *Cremoris, L. Lactis* Subsp. *Lactis*, or *L. raffinolactis*

According to in vitro studies, two important chemical reactions occurring in alcohol metabolism, i.e., ADH and ALDH, were evaluated in connection with the activities of ADH and ALDH by using a culture containing *L. chungangensis, L. fujiensis, L. lactis* subsp. *cremoris, L. lactis* subsp. *lactis*, or *L. raffinolactis*.

Figure 3:
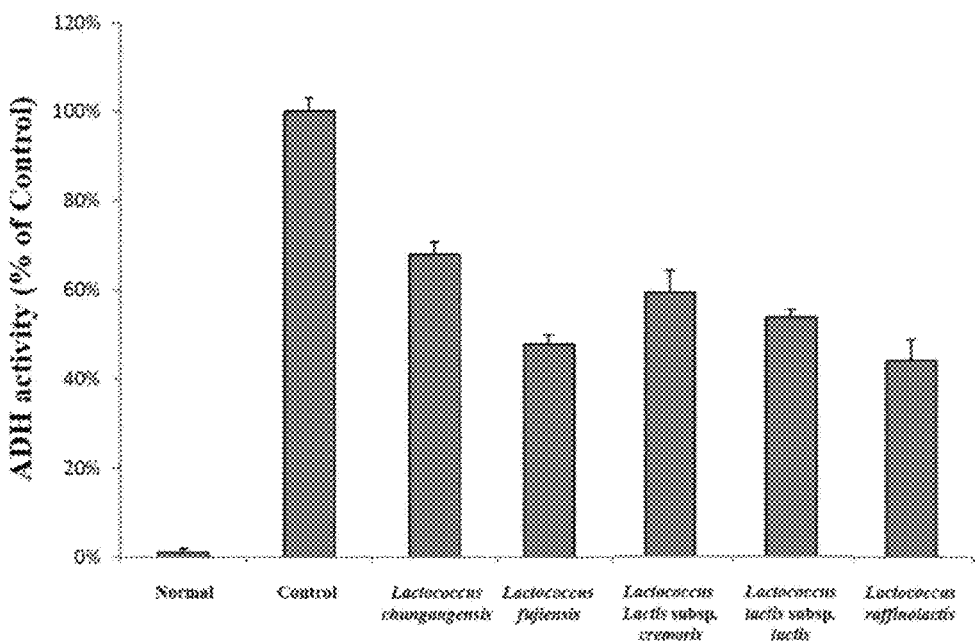
FIG. 3 is a graph showing measurements of alcohol dehydrogenase (ADH) activity on a culture containing *L. chungangensis, L. fujiensis, L. lactis* subsp. *cremoris, L. lactis* subsp. *lactis*, or *L. raffinolactis*, the measurements being obtained via an in vitro method.

As shown in FIG. 3, the result of the ADH activity in a culture containing *L. chungangensis* shows that the ADH activity in the culture containing *L. chungangensis* was lower than that in a control group, but had a high level of 66.6%. The result of the ADH activity in a culture containing

*L. fujiensis* shows that the ADH activity in the culture containing *L. fujiensis* was lower than that in a control group, but had a high level of 48.7%. The result of the ADH activity in a culture containing *L. lactis* subsp. *cremoris* shows that the ADH activity in the culture containing *L. lactis* subsp. *cremoris* was lower than that in a control group, but had a high level of 59.3%. The result of the ADH activity in a culture containing *L. lactis* subsp. *lactis* shows that the ADH activity in the culture containing *L. lactis* subsp. *lactis* was lower than that in a control group, but had a high level of 55.2%. The result of the ADH activity in a culture containing *L. raffinolactis* shows that the ADH activity in the culture containing *L. raffinolactis* was lower than that in a control group, but had a high level of 44.2%.

Figure 4:
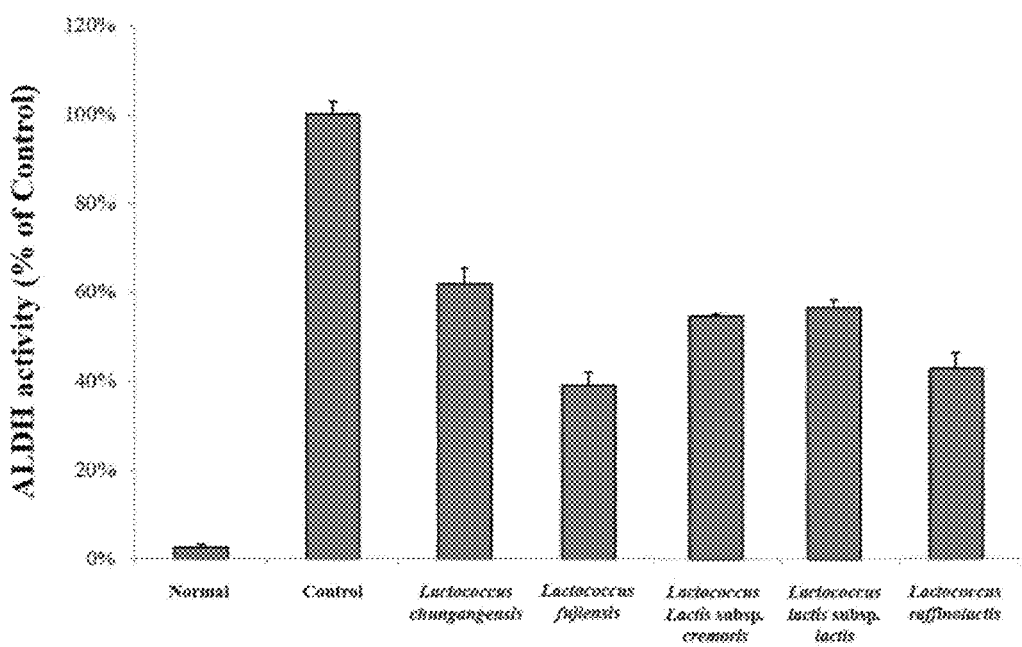
FIG. 4 is a graph showing measurements of acetaldehyde dehydrogenase (ALDH) activity on a culture containing *L. chungangensis, L. fujiensis, L. lactis* subsp. *cremoris, L. lactis* subsp. *lactis*, or *L. raffinolactis*, the measurements being obtained via an in vitro method.

In addition, as shown in FIG. 4, the result of the ALDH activity in a culture containing *L. chungangensis* shows that the ALDH activity in the culture containing *L. chungangensis* was lower than that in a control group, but had a high level of 62.8%. The ALDH activity in a culture containing *L. fujiensis* shows that the ALDH activity in the culture containing *L. fujiensis* was lower than that in a control group, but had a high level of 39.3%. The ALDH activity in a culture containing *L. lactis* subsp. *cremoris* shows that the ALDH activity in the culture containing *L. lactis* subsp. *cremoris* was lower than that in a control group, but had a high level of 53.4%. The ALDH activity in a culture containing (*L. lactis* subsp. *lactis* shows that the ALDH activity in the culture containing *L. lactis* subsp. *lactis* was lower than that in a control group, but had a high level of 58.3%. The result of the ALDH activity in a culture containing *L. raffinolactis* shows that the ALDH activity in the culture containing *L. raffinolactis* was lower than that in a control group, but had a high level of 43.9%.

The results above further extensively refer that *L. chungangensis, L. fujiensis, L. lactis* subsp. *cremoris, L. lactis* subsp. *lactis*, or *L. raffinolactis* can be possibly used as a functional food to help alleviation of hangovers and liver functions.

4. Measurement of ADH and ALDH Activity in Cream Cheese Prepared Using *L. chungangensis, L. Fujiensis, L. lactis* Subsp. *Cremoris, L. Lactis* Subsp. *Lactis*, or *L. raffinolactis*

According to in vitro studies, two important chemical reactions occurring in alcohol metabolism, i.e., ADH and ALDH, were evaluated in connection with the activities of ADH and ALDH by using cream cheese prepared using *L. chungangensis, L. fujiensis, L. lactis* subsp. *cremoris, L. lactis* subsp. *lactis*, or *L. raffinolactis*.

Figure 5:
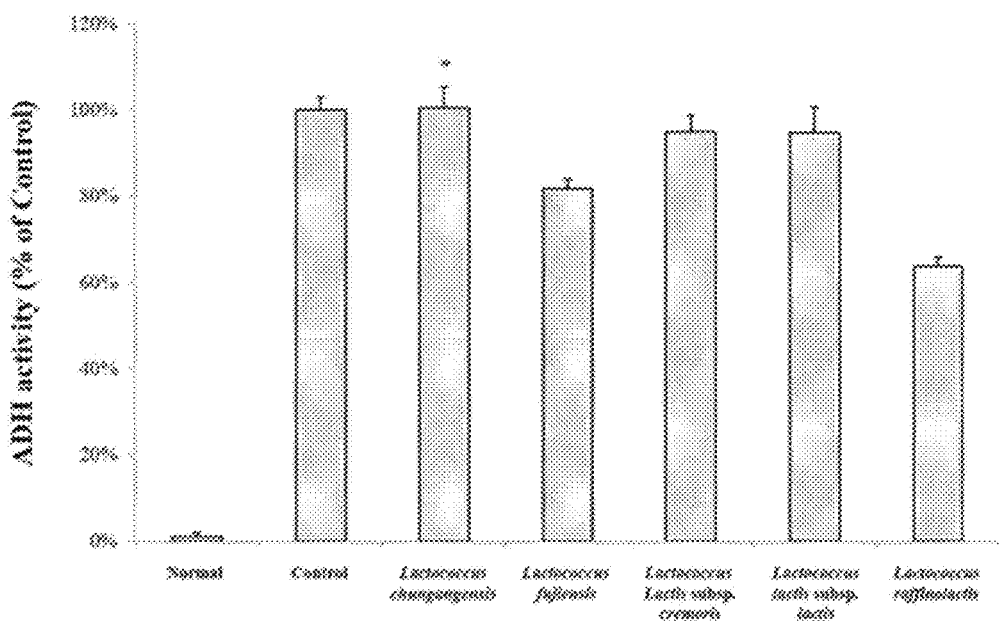
FIG. 5 is a graph showing ADH activity on cream cheese prepared using *L. chungangensis, L. fujiensis, L. lactis* subsp. *cremoris, L. lactis* subsp. *lactis*, or *L. raffinolactis*, the measurements being obtained via an in vitro method.

As shown in FIG. 5, the result of the ADH activity in cream cheese prepared using *L. chungangensis* shows that the ADH activity in cream cheese prepared using *L. chungangensis* was higher than that of a control group by 0.4%. The result of the ADH activity in cream cheese prepared using *L. fujiensis* shows that ADH activity in cream cheese prepared using *L. fujiensis* had a high level of 81.7%, compared with the ADH activity in a control group. The result of the ADH activity in cream cheese prepared using *L. lactis* subsp. *cremoris* shows that ADH activity in cream cheese prepared using *L. lactis* subsp. *cremoris* had a high level of 94.9%, compared with the ADH activity in a control group. The result of the ADH activity in cream cheese prepared using *L. lactis* subsp. *lactis* shows that ADH activity in cream cheese prepared using *L. lactis* subsp. *lactis* had a high level of 94.8%, compared with the ADH activity in a control group. The result of the ADH activity in cream cheese prepared using *L. raffinolactis* shows that ADH activity in cream cheese prepared using *L. raffinolactis* had a high level of 63.8%, compared with the ADH activity in a control group.

Figure 6:
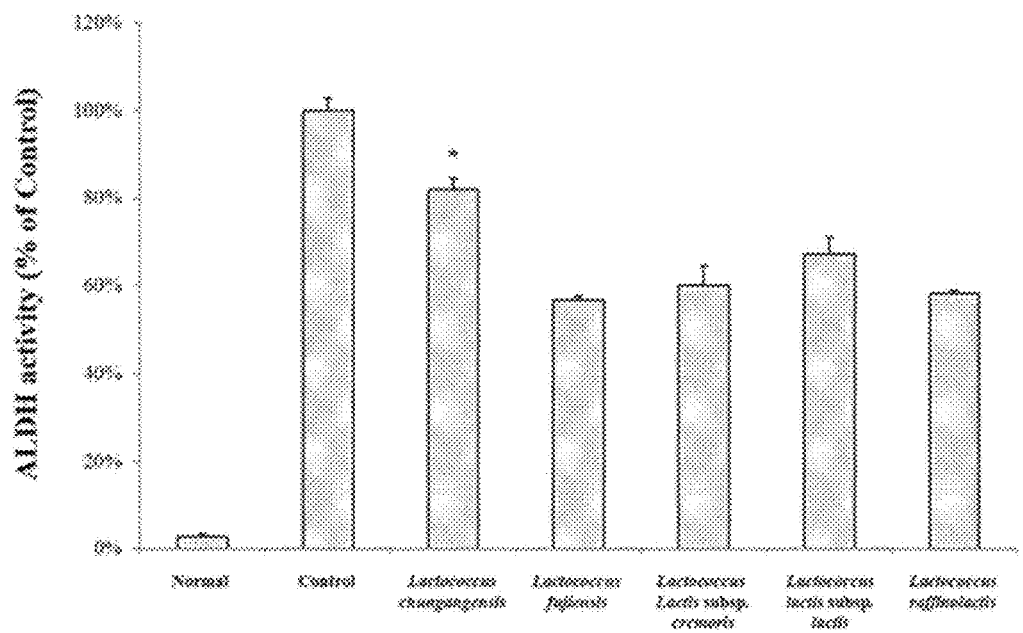
FIG. 6 is a graph showing measurements ALDH activity on cream cheese prepared using *L. chungangensis, L. fujiensis, L. lactis* subsp. *cremoris, L. lactis* subsp. *lactis*, or *L. raffinolactis*, the measurements being obtained via an in vitro method.
Figure 7A:
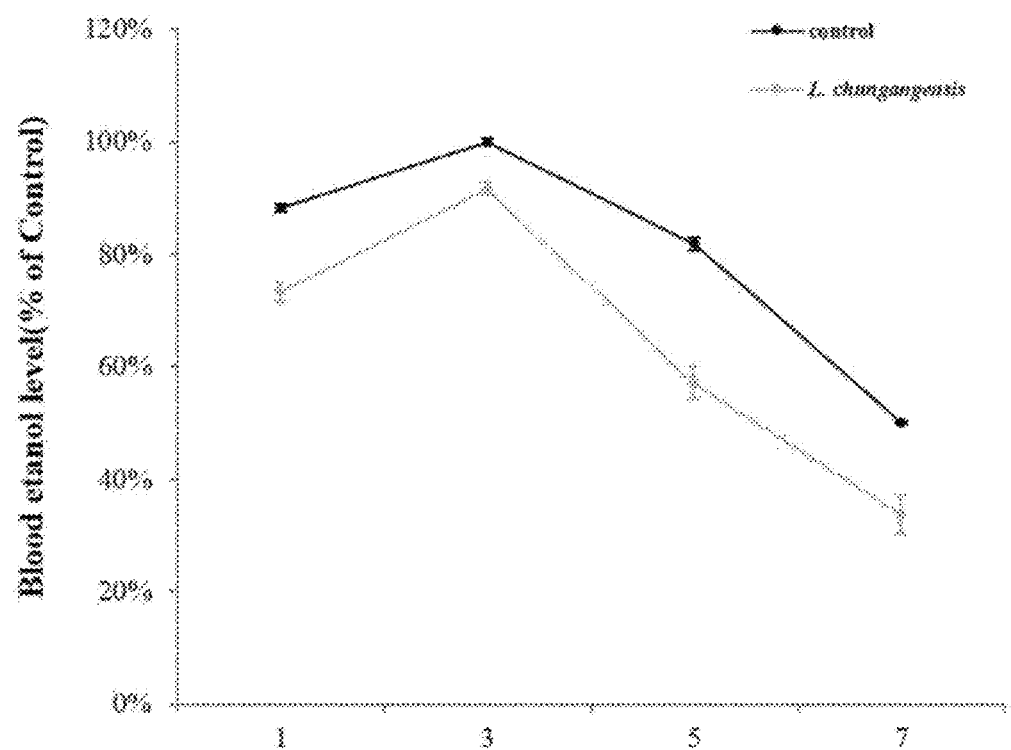
FIGS. 7A to 7E are graphs showing blood ethanol levels in mice to which cream cheese preparing using *L. chungangensis, L. fujiensis, L. lactis* subsp. *cremoris, L. lactis* subsp. *lactis*, or *L. raffinolactis* is orally administered.
Figure 7B:
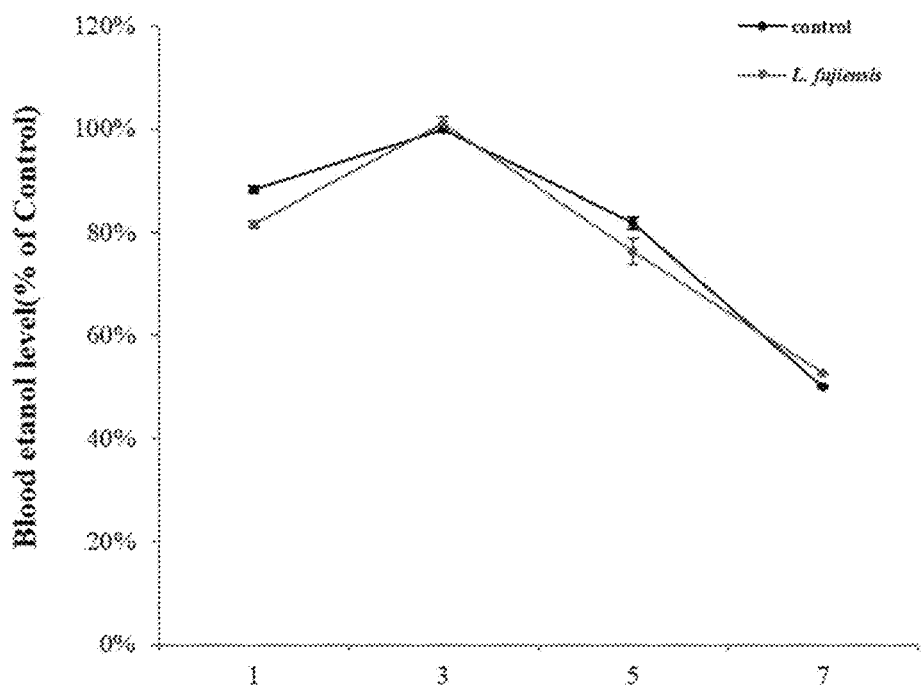
Figure 7C:
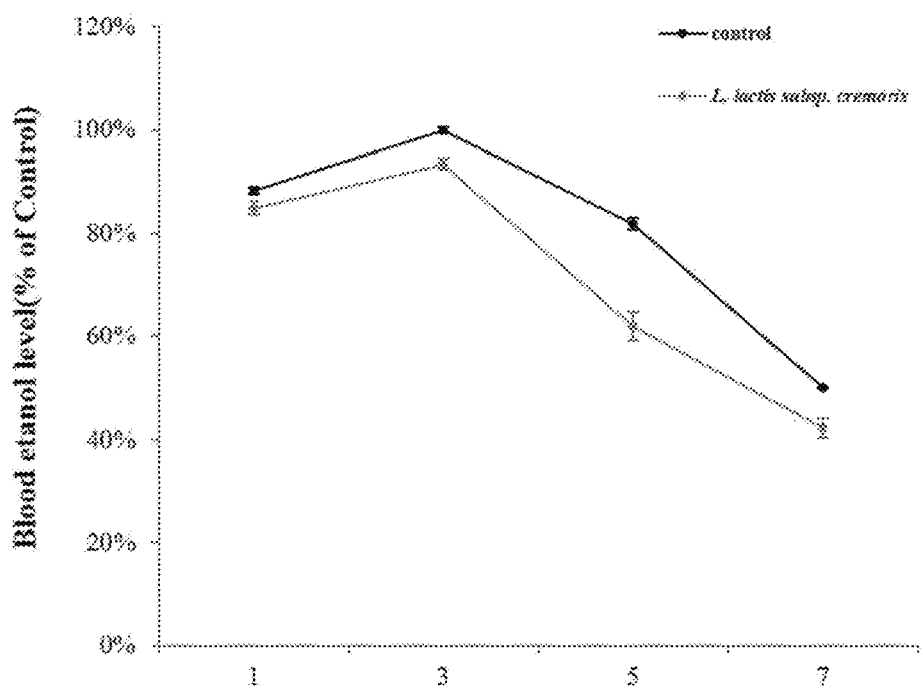
Figure 7D:
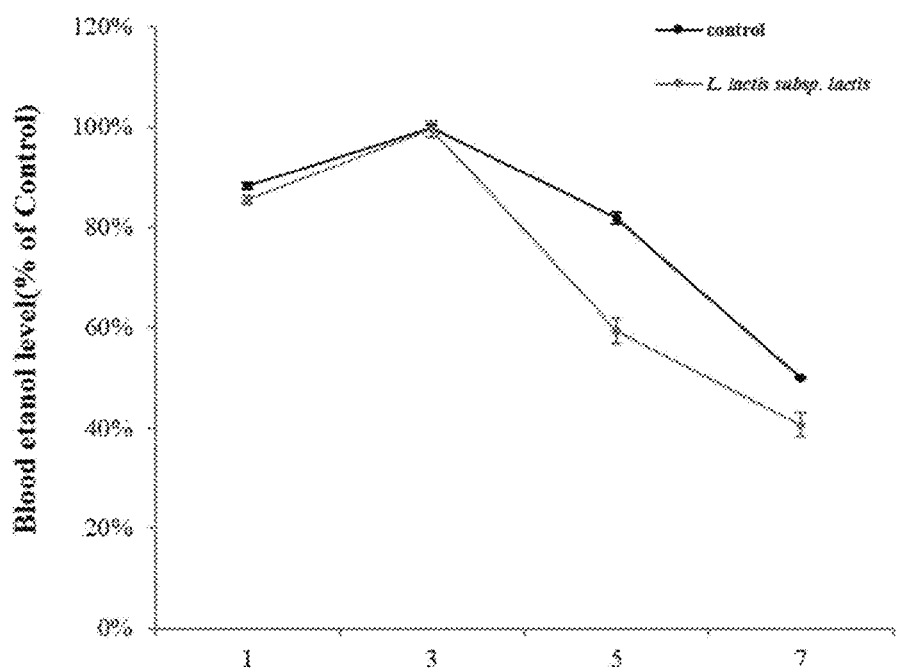
Figure 7E:
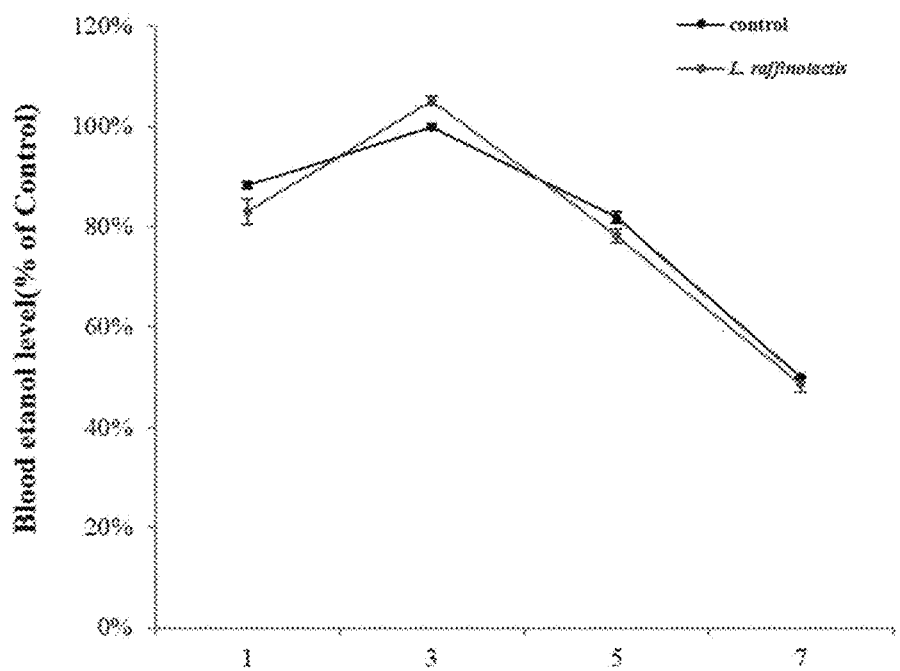
Figure 8A:
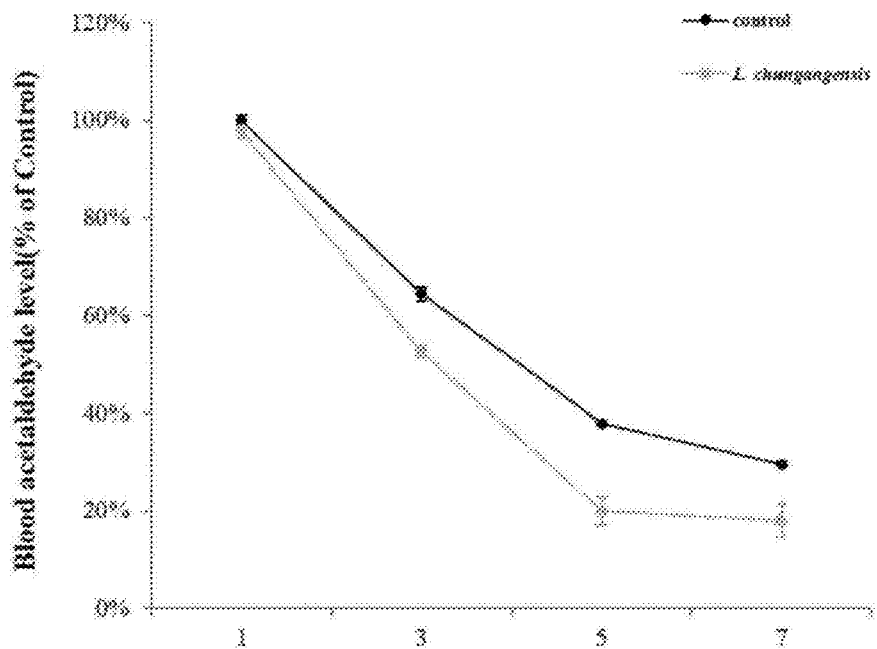
FIGS. 8A to 8E are graphs showing blood acetaldehyde level in mice to which cream cheese preparing using *L. chungangensis, L. fujiensis, L. lactis* subsp. *cremoris, L. lactis* subsp. *lactis*, or *L. raffinolactis* is orally administered.
Figure 8B:
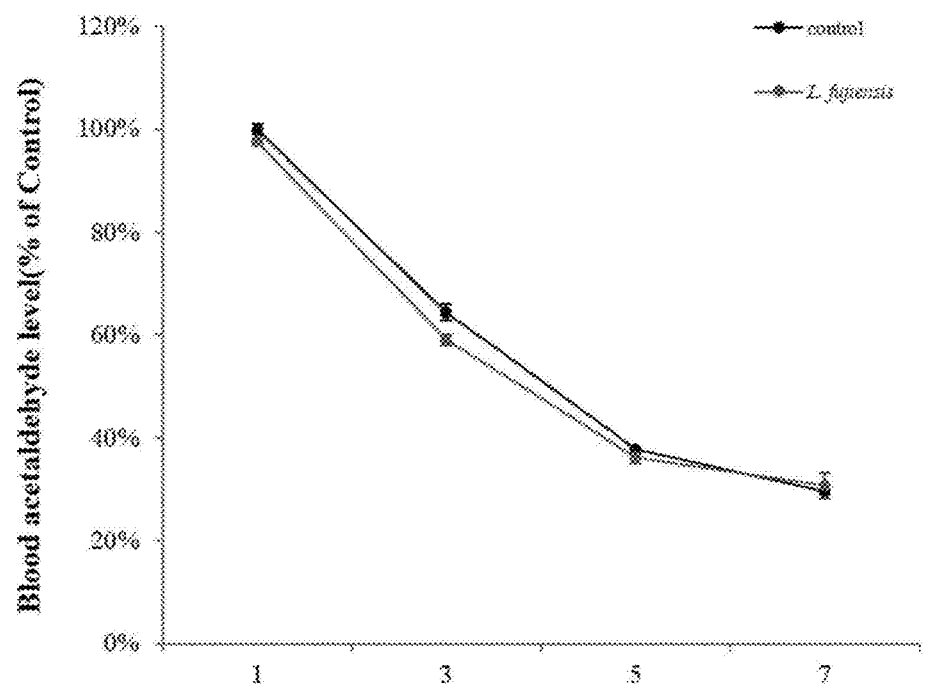
Figure 8C:
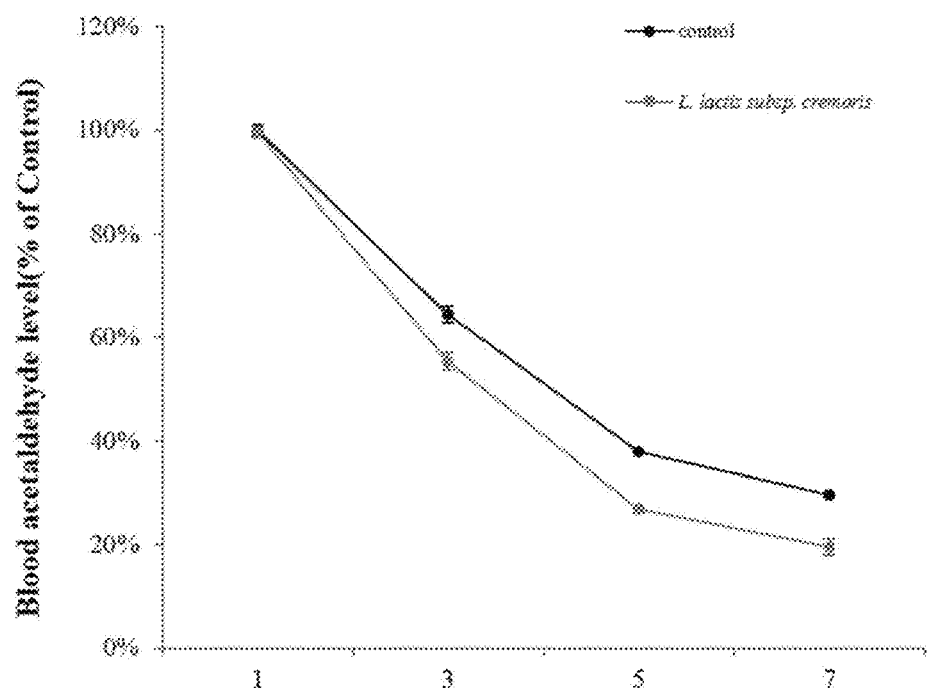
Figure 8D:
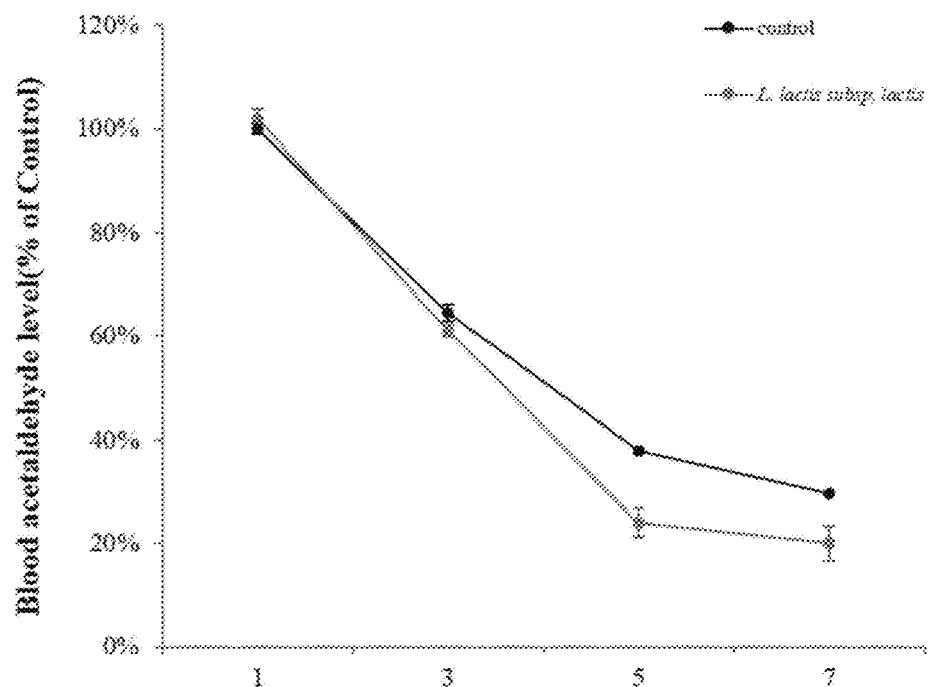
Figure 8E:
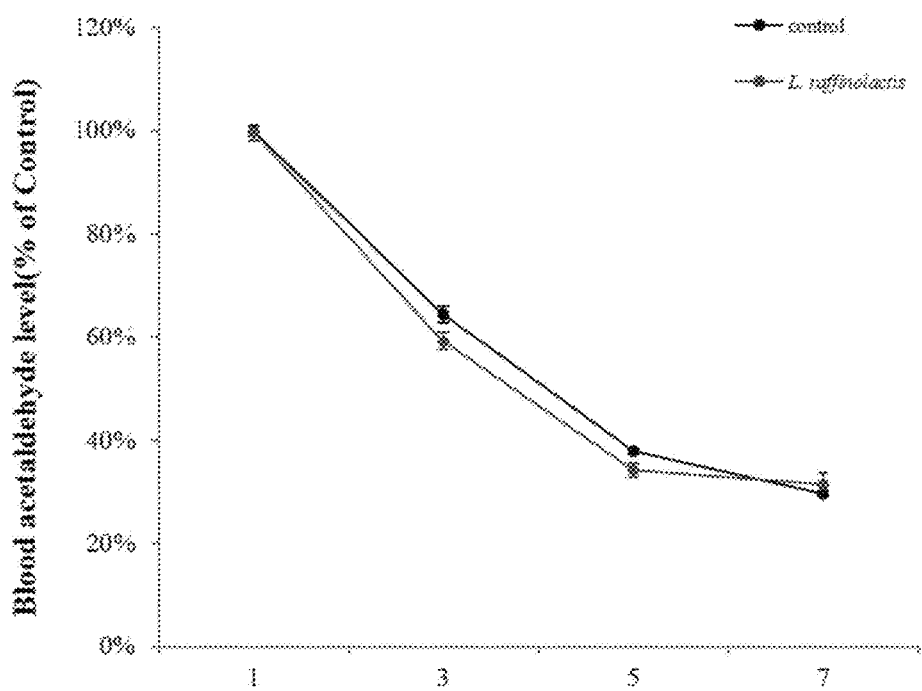

In addition, as shown in FIG. 6, the result of ALDH activity in cream cheese prepared using *L. chungangensis* shows that the ADH activity in cream cheese prepared using *L. chungangensis* was lower than that in a control group, but had a high level of 82.1%. The result of the ALDH activity in cream cheese prepared using *L. fujiensis* shows that ALDH activity in cream cheese prepared using *L. fujiensis* had a high level of 56.8%, compared with the ALDH activity in a control group. The result of the ALDH activity in cream cheese prepared using *L. lactis* subsp. *cremoris* shows that ALDH activity in cream cheese prepared using *L. lactis* subsp. *cremoris* had a high level of 60.1%, compared with the ALDH activity in a control group. The result of the ALDH activity in cream cheese prepared using *L. lactis* subsp. *lactis* shows that ALDH activity in cream cheese prepared using *L. lactis* subsp. *lactis* had a high level of 67.3%, compared with the ALDH activity in a control group. The result of the ALDH activity in cream cheese prepared using *L. raffinolactis* shows that ALDH activity in cream cheese prepared using *L. raffinolactis* had a high level of 58.1%, compared with the ALDH activity in a control group.

That is, regarding comparative evaluation between cream cheese prepared using *L. fujiensis* and cream cheese prepared using *L. chungangensis*, the ADH activity of *L. chungangensis* was higher than that of *L. fujiensis* by 18.7%. In addition, the ALDH activity of *L. chungangensis* was higher than that of *L. fujiensis* by 25.3%.

Regarding comparative evaluation between cream cheese prepared using *L. lactis* subsp. *cremoris* and cream cheese prepared using *L. chungangensis*, the ADH activity of *L. chungangensis* was higher than that of *L. lactis* subsp. *cremoris* by 5.5%. In addition, the ALDH activity of *L. chungangensis* was higher than that of *L. lactis* subsp. *cremoris* by 22.0%.

Regarding comparative evaluation between cream cheese prepared using *L. lactis* subsp. *lactis* and cream cheese prepared using *L. chungangensis*, the ADH activity of *L. chungangensis* was higher than that of *L. lactis* subsp. *lactis* by 5.6%. In addition, the ALDH activity of *L. chungangensis* was higher than that of *L. lactis* subsp. *lactis* by 14.8%.

Regarding comparative evaluation between cream cheese prepared using *L. raffinolactis* and cream cheese prepared using *L. chungangensis*, the ADH activity of *L. chungangensis* was higher than that of *L. raffinolactis* by 36.6%. In addition, ALDH activity of *L. chungangensis* was higher than that of *L. raffinolactis* by 24.0%.

*L. chungangensis* was found to be easily used as a cream cheese starter which can decompose ethanol like cream cheese does, and cream cheese prepared using *L. fujiensis, L. lactis* subsp. *cremoris, L. lactis* subsp. *lactis*, or *L. raffinolactis* was found to be possibly used as a functional food to help alleviation of hangovers and liver functions.

5. Measurement of Concentrations of Alcohol and Acetaldehyde in Mouse by Oral Administration of Cream Cheese Prepared Using *L. Chungangensis, L. Fujiensis, L. lactis* Subsp. *Cremoris, L. Lactis* Subsp. *Lactis*, or *L. raffinolactis*

To confirm the effect of cream cheese prepared using *L. chungangensis, L. fujiensis, L. lactis* subsp. *cremoris, L. lactis* subsp. *lactis*, or *L. raffinolactis* on alleviation of hangovers, a white mouse was used to measure the concentrations of blood alcohol and acetaldehyde. As shown in FIG. 7, the blood alcohol (ethanol) level peaked at 3 hours after drinking, and it was confirmed that a group in which alcohol was taken along with cream cheese prepared using

*L. chungangensis* showed a decreased alcohol level by 25% at 5 hours after drinking, compared with a group in which alcohol was taken alone. In addition, it was confirmed that a group in which alcohol was taken along with cream cheese prepared using *L. fujiensis* showed a decreased alcohol level by 6% at 5 hours after drinking, compared with a group in which alcohol was taken alone. In addition, it was confirmed that a group in which alcohol was taken along with cream cheese prepared using *L. lactis* subsp. *cremoris* showed a decreased alcohol level by 20% at 5 hours after drinking, compared with a group in which alcohol was taken alone. In addition, it was confirmed that a group in which alcohol was taken along with cream cheese prepared using *L. lactis* subsp. *lactis* showed a decreased alcohol level by 23% at 5 hours after drinking, compared with a group in which alcohol was taken alone. In addition, it was confirmed that a group in which alcohol was taken along with cream cheese prepared using *L. raffinolactis* showed a decreased alcohol level by 4% at 5 hours after drinking, compared with a group in which alcohol was taken alone.

In addition, as shown in FIG. 8, the blood acetaldehyde level peaked at 1 hour after drinking, and it was confirmed that a group in which alcohol was taken along with cream cheese prepared using *L. chungangensis* showed a decreased acetaldehyde level by 18% at 5 hours after drinking, compared with a group in which alcohol was taken alone. In addition, it was confirmed that a group in which alcohol was taken along with cream cheese prepared using *L. fujiensis* showed a decreased acetaldehyde by 2% at 5 hours after drinking, compared with a group in which alcohol was taken alone. In addition, it was confirmed that a group in which alcohol was taken along with cream cheese prepared using *L. lactis* subsp. *cremoris* showed a decreased acetaldehyde by 11% at 5 hours after drinking, compared with a group in which alcohol was taken alone. In addition, it was confirmed that a group in which alcohol was taken along with cream cheese prepared using *L. lactis* subsp. *lactis* showed a decreased acetaldehyde by 14% at 5 hours after drinking, compared with a group in which alcohol was taken alone. In addition, it was confirmed that a group in which alcohol was taken along with cream cheese prepared using *L. raffinolactis* showed a decreased acetaldehyde by 4% at 5 hours after drinking, compared with a group in which alcohol was taken alone.

Based on the results above, cream cheese prepared using *L. chungangensis*, *L. fujiensis*, *L. lactis* subsp. *cremoris*, *L. lactis* subsp. *lactis*, or *L. raffinolactis* was found to lower the concentration of blood acetaldehyde, which is known as a major cause of hangovers, and thus, such cream cheese is considered to be able to reduce harmful symptoms appearing in the body after alcohol consumption, and to be possibly used as a functional food.

The invention claimed is:

1. A method for alleviating hangovers in a subject in need thereof, comprising:
   administering to the subject a food composition comprising *Lactococcus chungangensis* (KCTC12684BP), or a culture medium thereof in an amount effective to alleviate the hangovers.

2. The method of claim 1, wherein the food composition further comprises at least one strain selected from the group consisting of *Lactococcus fujiensis, Lactococcus lactis* subsp. *cremoris, Lactococcus lactis* subsp. *lactis*, and *Lactococcus raffinolactis*, or a culture medium thereof.

3. The method of claim 1, wherein the food composition is characterized by an acetaldehyde decomposition activity.

4. The method of claim 1, wherein the food is characterized by cheese, yogurt, butter, cream, ice cream, lactic acid beverage, kefir, kimchi, or dairy products.

5. The method of claim 4, wherein the cheese is characterized by cream cheese.

6. A method of preparing cream cheese for alleviating hangovers, the method comprising: (1) culturing *Lactococcus chungangensis* (KCTC1284BP), or a culture medium thereof, by inoculation into milk; (2) performing pasteurization on the culture cultured in step (1); (3) mixing the pasteurized culture with milk and heating the mixture; and (4) removing moisture from cheese obtained by the heating of the mixture.

7. The method of claim 6, wherein the step (1) further cultures at least one strain selected from the group consisting of *Lactococcus fujiensis, Lactococcus lactis* subsp. *cremoris, Lactococcus lactis* subsp. *lactis*, and *Lactococcus raffinolactis*, or a culture medium thereof.

8. The method of claim 1, wherein the food composition is characterized by an ethanol decomposition activity.

9. The method of claim 2, wherein the food composition is characterized by an ethanol decomposition activity.

10. The method of claim 2, wherein the food composition is characterized by an acetaldehyde decomposition activity.

11. The method of claim 2, wherein the food is characterized by cheese, yogurt, butter, cream, ice cream, lactic acid beverage, kefir, kimchi, or dairy products.

12. The method of claim 11, wherein the cheese is characterized by cream cheese.

\* \* \* \* \*